US006328684B1

(12) United States Patent
Ardizzone

(10) Patent No.: US 6,328,684 B1
(45) Date of Patent: *Dec. 11, 2001

(54) FLEXIBLE MAGNETIC PAD WITH MULTI-DIRECTIONAL CONSTANTLY ALTERNATING POLARITY ZONES

(75) Inventor: Vincent Ardizzone, Bay Shore, NY (US)

(73) Assignee: Nu-Magnetics, Inc., Port Jefferson, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/212,737

(22) Filed: Dec. 15, 1998

Related U.S. Application Data

(63) Continuation of application No. 08/678,348, filed on Jul. 11, 1996, now Pat. No. 5,871,438, which is a continuation-in-part of application No. 08/573,390, filed on Dec. 15, 1995, now Pat. No. 5,538,495, which is a continuation of application No. 08/427,733, filed on Apr. 24, 1995, now Pat. No. 5,514,072, which is a continuation of application No. 08/276,876, filed on Jul. 18, 1994, now abandoned, which is a continuation of application No. 08/158,607, filed on Nov. 29, 1993, now abandoned, which is a continuation of application No. 07/990,927, filed on Dec. 14, 1992, now Pat. No. 5,227,692, which is a continuation of application No. 07/823,149, filed on Jan. 21, 1992, now abandoned.

(51) Int. Cl.$^7$ .................................................. A61B 17/52
(52) U.S. Cl. .................................................. 600/9; 600/15
(58) Field of Search .................................. 600/9–15, 26

(56) References Cited

U.S. PATENT DOCUMENTS

| 4,549,532 | * | 10/1985 | Baermann | 600/9 |
| 5,277,692 | * | 1/1994 | Ardizzone | 600/9 |
| 5,304,111 | * | 4/1994 | Mitsuno et al. | 600/9 |
| 5,984,856 | * | 11/1999 | Love | 600/15 |

FOREIGN PATENT DOCUMENTS 2196855  5/1988  (GB) .............................. A61N/1/42

OTHER PUBLICATIONS

Horst M. Baermann; *The Influence Of Multipolar Static Magnetic Fields On The Electrolytic System Of The Living Organism With Special Reference To Circular And Radial Pole Patterns;* This paper was presented at the International Symposium Biomagnetology, Magnetotherapy and Postural Activity, Newport, R.I. USA, May 29, 1989.

\* cited by examiner

*Primary Examiner*—Brian L. Casler
(74) *Attorney, Agent, or Firm*—Cislo & Thomas LLP

(57) ABSTRACT

A flexible magnetic pad is provided with constantly alternating polarity zones which therapeutically effect blood vessels to increase blood flow, irrespective of the orientation of any blood vessel with respect to the pad, the polarity zones being arranged in an alternating pattern throughout the pad.

13 Claims, 6 Drawing Sheets

FIG.11 form of FIGS. 1, 3 and 4, the device is effective only in an area including and proximal to the center of the pad. Baermann '532 radial sector configuration is effective only in a peripheral area of the pad.

FLEXIBLE MAGNETIC PAD WITH MULTI-DIRECTIONAL CONSTANTLY ALTERNATING POLARITY ZONES

CROSS-REFERENCES TO RELATED APPLICATIONS

This is a continuation of application Ser. No. 08/678,348 filed Jul. 11, 1996, now U.S. Pat. No. 5,871,438 which is a continuation in part of application Ser. No. 08/573,390 filed Dec. 15, 1995, now U.S. Pat. No. 5,538,495, which is a continuation of application Ser. No. 08/427,733 filed Apr. 24, 1995, now U.S. Pat. No. 5,514,072, which is a continuation of application Ser. No. 08/276,876 filed Jul. 18, 1994, now abandoned, which is a continuation of application Ser. No. 08/158,607 filed Nov. 29, 1993, now abandoned, which is a continuation of application Ser. No. 07/990,927 filed Dec. 14, 1992, now U.S. Pat. No. 5,277,692, which is a continuation of application Ser. No. 07/823,149 filed Jan. 21, 1992, now abandoned, all of which are incorporated herein by this reference.

A flexible magnetic pad is provided with constantly alternating polarity zones which therapeutically affects blood vessels to increase blood flow, irrespective of the orientation of the blood vessels with respect to the pad. In the preferred embodiment, the polarity zones are tightly wound in alternating poles arranged in a spiral configuration throughout the pad.

BACKGROUND OF THE INVENTION

Various attempts have been made to provide therapeutic pads with magnetic alternating polarities to increase blood flow and therefore, accelerate healing of injured body parts. The technology is based on principles of electricity and magnetism set forth in Faraday's Law of Magnetic Induction and the Hall Effect. Basically, these principles establish the fact that charged particles experience a force acting upon them when they move through a magnetic field in a perpendicular direction. Since human blood is replete with ions and electrolytes, it is an ideal carrier of charged particles. A blood vessel exposed to a proper alignment of alternating magnetic fields could experience an induced voltage of sufficient strength to produce a mild alternating current which could generate enough heat to cause a widening of the blood vessel and thus an increase in blood flow.

In U.S. Pat. No. 4,489,711 of Latzke, alternating stripes of north and south magnetic poles are unidirectional in pole orientation. Latzke '711 provides parallel stripe-shaped poles in a linear arrangement that do not exhibit therapeutic effects on blood vessels that are not extending substantially transversely thereto.

In U.S. Pat. No. 4,549,532 of Baermann either concentric rings or radial sectors with alternating polarities are provided. However, with respect to the concentric ring configuration of Baermann '532, the effective orientation for the concentric ring design is limited because of the assumption that all blood vessels will cross through the center of the device. The Baermann '532 device becomes progressively less effective as blood vessels are positioned away from the center until the device is non-effective at its peripheral outer ring, where a blood vessel will only transverse one pole with no increase in blood flow. The reverse is true for the radial sector configuration of Baermann '532 where the device's effectiveness decreases as blood vessels are positioned away from the periphery and toward the center. The Baermann '532 Patent states that the concentric ring device, which is his preferred embodiment, can be universally oriented on a body site. However, the Baermann '532 "body site" is limited to an area where blood vessels traverse across the center of the device and therefore the therapeutic effects of the magnetic pad on the blood vessels covered by the area of the pad is diminished because of the necessity for all blood vessels to traverse the center.

The advantage of the placement of the present invention is that it takes into account all random positions of the blood vessels relative to the location of the device. The present invention maximizes the effective area underneath the pad. It works as well for a blood vessel traversing near the periphery as it does for a blood vessel traversing the center of the pad.

The device of the present invention is made from a ferrite material which is magnetized and impregnated within a rubbery synthetic material. With the present invention, more varied orientations of alternating polarities of magnetic poles with respect to the body site blood vessels are accomplished in a spiral orientation, which insures that blood vessels must cross alternating poles at any angle or position across the therapeutic pad.

In the present invention, the poles of the same polarity are in staggered positions, which means that no two poles of the same polarity are adjacent to each other. The present invention insures that blood vessels crossing a pole of one polarity will cross another pole of opposite polarity without exceeding the effective therapeutic distance between poles of 4 to 10 mm, as claimed in the Latzke '711 patent. Specifically, Latzke '711 states at column 3, lines 9–13, that magnetic sheets having alternating positive and negative poles in strips 2 mm apart, are too close for therapeutic purposes. Latzke '711 further states at column 3, lines 13–18, that strips of alternating polarity 5 mm are especially satisfactory.

A study by Dr. Ted Zablotsky of October, 1989 entitled "The Activation of Permanent Magnets in Musculoskeletal Injuries" in undated commercial literature entitled "The Science of Biomagnetics," discusses the Baermann '532 patent and alleges on page 19, line 2 and 3 that "every blood vessel" except for those perpendicular to the skin, will cross a series of north and south Poles. Zablotsky illustrates his theory with a drawing FIG. 3 on page 19 thereof, which shows three ideal blood vessel positions across the Baermann '532 device, where the vessel is located close to or at the center of the pad. In reality, however, this ideal arrangement of blood vessels cannot be expected.

In short, the Baermann '532 device has no poles which alternate circumferentially, except for an alternate embodiment with "pie piece" shaped sectors adjacent to each other in a radial arrangement. However, this alternate embodiment of the Baermann '532 device is only effective near the peripheral areas of the device, since a blood vessel traversing at or near the center of the pad will substantially pass only through one polarity, crossing the pad from "north to north" or "south to south only.

As mentioned, the aforesaid Latzke '711 patent claims an effective therapeutic range in pole width of each pole of 4 to 10 millimeters. Therefore, the Baermann '532 device cannot overcome the limitations of the concentric ring design by adding more rings in a more densely packed arrangement since decreasing the width of the rings to less than 4 mm would be of no therapeutic value. Therefore, the Baermann '532 device is limited in the number of rings used in the device since the width of the rings must decrease as the number of rings increases.

To summarize, in the Baermann '532 device having concentric ring versions shown in FIGS. 1, 3 and 4 in the Baermann '532 patent (and illustrated herein as drawing FIGS. 5 & 6), the Baermann '532 magnetic impregnated pad has a decreasing effect as the orientation of the blood vessel leaves the center of the pad and approaches the periphery of the pad where it will not be exposed to alternating polarities.

Likewise, in the Baermann '532 pie sector version shown in FIG. 2 (and illustrated in drawing FIGS. 7 & 8 herein), the pad therein will have decreasing effect on blood vessel flow as the orientation of the blood vessel leaves the periphery and approaches the center where it will not be exposed to alternating polarities.

SUMMARY OF THE INVENTION

The device of the present invention utilizes principles set forth in the Latzke '711. In the present invention, magnetic poles are arranged in an alternating pattern of north (−) and south (+) polarity zones or poles. When placed over an afflicted area of the human body, these polarity zones have been shown to have a therapeutic effect. For example, the pad can be applied to musculo-skeletal bruises, sore muscles and joint pain for relief to the user from such pain. These polarity zones, however, must be positioned in such a way as to cause blood moving through the veins in the body to pass through the magnetic fields established by the polarity zones in an alternating field pattern. This would easily be accomplished if all the blood vessels in the body were situated in the same direction. It is obvious, however, that this is not the case. The Latzke '711 device calls for the magnetic poles to be arranged a parallel-striped configuration, as noted in FIG. 1 of Latzke '711 (as illustrated in FIGS. 3 and 4 herein). Therefore, its effectiveness is limited only to those blood vessels which cross the parallel boundaries of adjacent poles in a perpendicular or nearly perpendicular manner (as noted in FIG. 4 herein of the present invention).

In an attempt to overcome this limitation, the Baermann '532 patent proposed that the alternating magnetic poles be arranged in a concentric ring configuration as noted in Baermann '532 FIG. 3 therein. At first glance, it would appear that this configuration of the Baermann '532 patent should be effective on blood vessels in any orientation in the body. However, upon to closer examination it becomes clear that the Baermann '532 configuration is effective only on those blood vessels which cross at or near the center of the pole configuration (as noted in FIG. 6 herein). Although the Baermann '532 configuration affects more blood vessels than the Latzke '711 configuration and therefore represents an improvement over the Latzke device, it does not offer the optimum configuration to deal with all possible blood vessel orientations in the body with respect to the device.

To overcome the limitation of the previous patents described above, the present invention provides a new configuration which does in fact affect blood vessels in any orientation in the body under which the device is placed. This present invention includes a pattern of constantly alternating polarity zones, preferably in a spiral configuration, arranged in such a way as to produce magnetic fields which alternate radially as well as circumferentially. It can be clearly shown that no matter how blood vessels are situated under the present invention, that they must cross through alternating magnetic fields and therefore receive an optimal effect. Even though a blood vessel might cross near the periphery of the device it still passes through several alternating magnetic fields and therefore experiences an optimal effect. Furthermore, the average distance between poles remains relatively constant whereas with the Baermann '532 device the distance which blood must travel before passing through alternating magnetic fields varies dramatically for those blood vessels not situated across the center of the device, thus minimizing its effectiveness.

In a further preferred embodiment, magnetic zones of north polarity and magnetic zones of south polarity are positioned contiguous one another with at least one magnetic zone of north polarity being contiguous with four zones of south polarity and with at least one magnetic zone of south polarity being contiguous with four zones of north polarity.

Considering the differences in functionality and configuration between the proposed device and that of the prior art, the proposed device of the present invention is an improvement over the prior art that is substantial and not obvious.

OBJECTS OF THE INVENTION

Therefore, it is an object of the present invention to provide a therapeutic magnetic pad of constantly alternating polarity zones which is effective no matter where a blood vessel traverses the pad.

It is a further object to improve over the disadvantages of the prior art.

BRIEF DESCRIPTION OF THE DRAWINGS

FIGS. 9–11 are alternate embodiments of the present invention.

DETAILED DESCRIPTION OF THE PREFERRED EMBODIMENT

Figure 1:
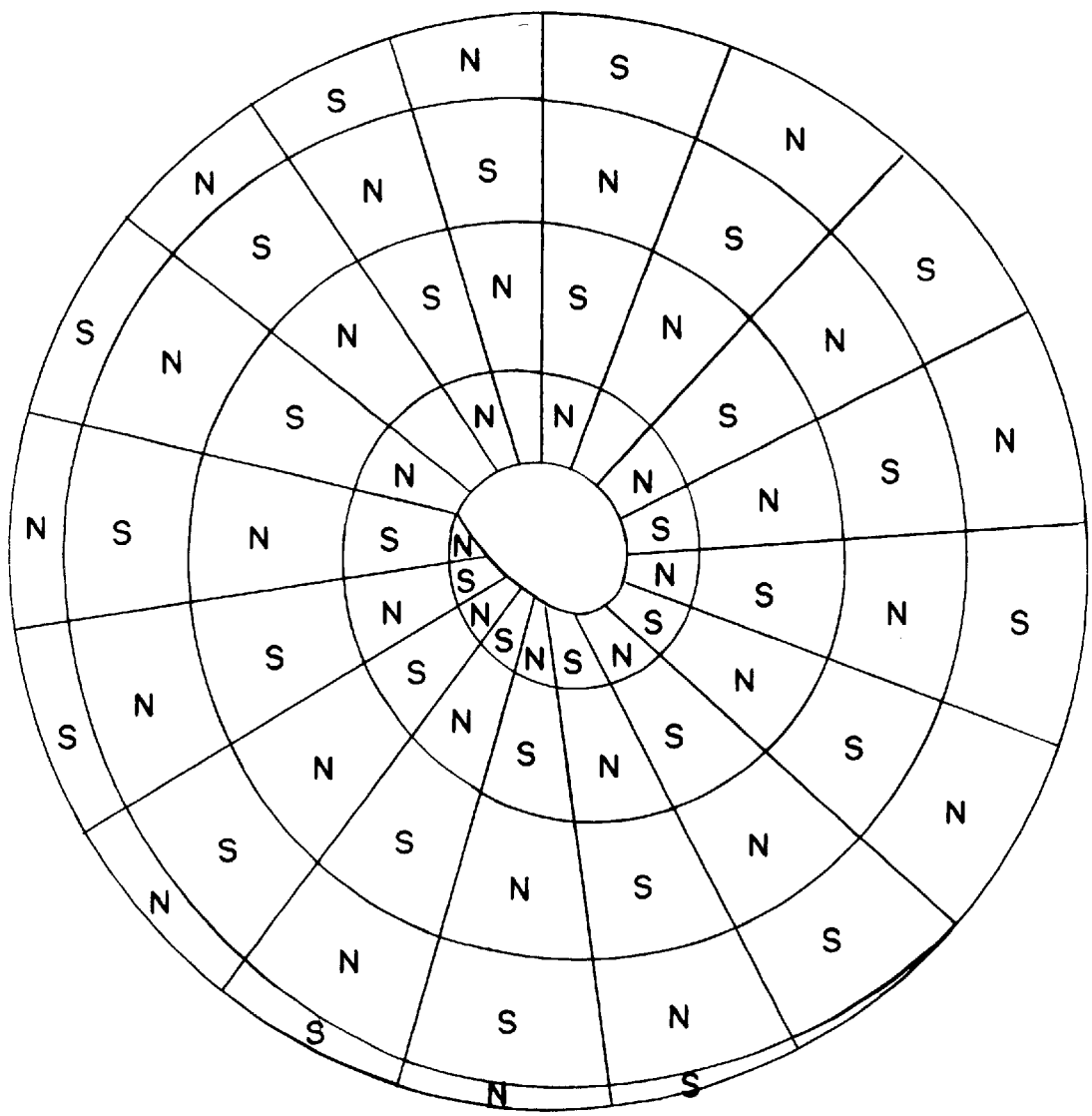
FIG. 1 is a top plan view of the device.

As noted in FIG. 1, there is provided a flexible magnetic pad 10 having alternating north and south polarity zones denoted by reference numerals 12 and 14. The alternating polarity zones 12 and 14 are arranged in preferably a spiral pattern emanating from the center 16 of the device.

As such, no two polarity zones 12 and 14 are adjacent to any other polarity zones of the same polarity. For example, the north polarity zone 12 is always adjacent to south polarity zones 14, 14a and 14b. Likewise, south polarity zone 14 is always adjacent to north polarity zones 12, 12a and 12b throughout the spiral configuration as shown in FIG. 1.

Figure 2:
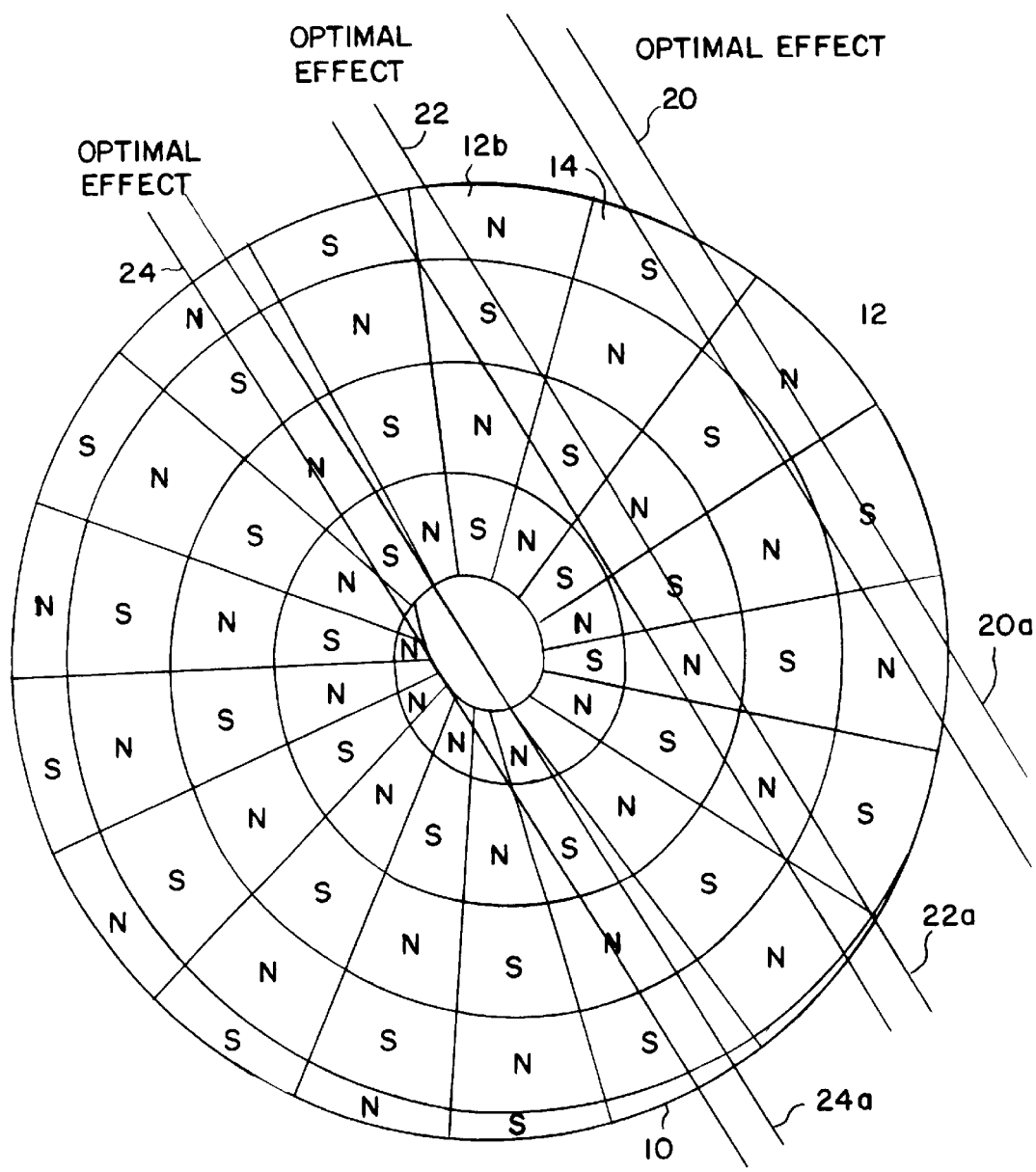
FIG. 2 is a top plan view of the device as in FIG. 1, showing various positions of blood vessels traversing the device of the present invention.

As shown in FIG. 2, there are three possible orientations of blood vessels traversing the magnetic pad of the present device at three positions 20, 22 and 24 representing the peripheral, off-center, and center crossing paths of the device respectively. Note that these positions can be at any angle, although only one angle is shown here for clarity. Blood vessels 20a, 22a, and 24a are shown as oriented along positions 20, 22, and 24 respectively.

As noted in FIG. 2, blood vessel 20a at the periphery along path 20 will always traverse alternating north and south polarity zones, and therefore experiences an increase in blood flow. Furthermore, the same optimal exposure to alternate polarities occurs in blood vessel 22a which traverses along position 22 and blood vessel 24a which traverses along position 24. Note that although blood vessel 20a crosses fewer alternating poles than do blood vessels 22a and 24a, it still crosses enough alternating poles to receive the desired effect.

Figure 4:
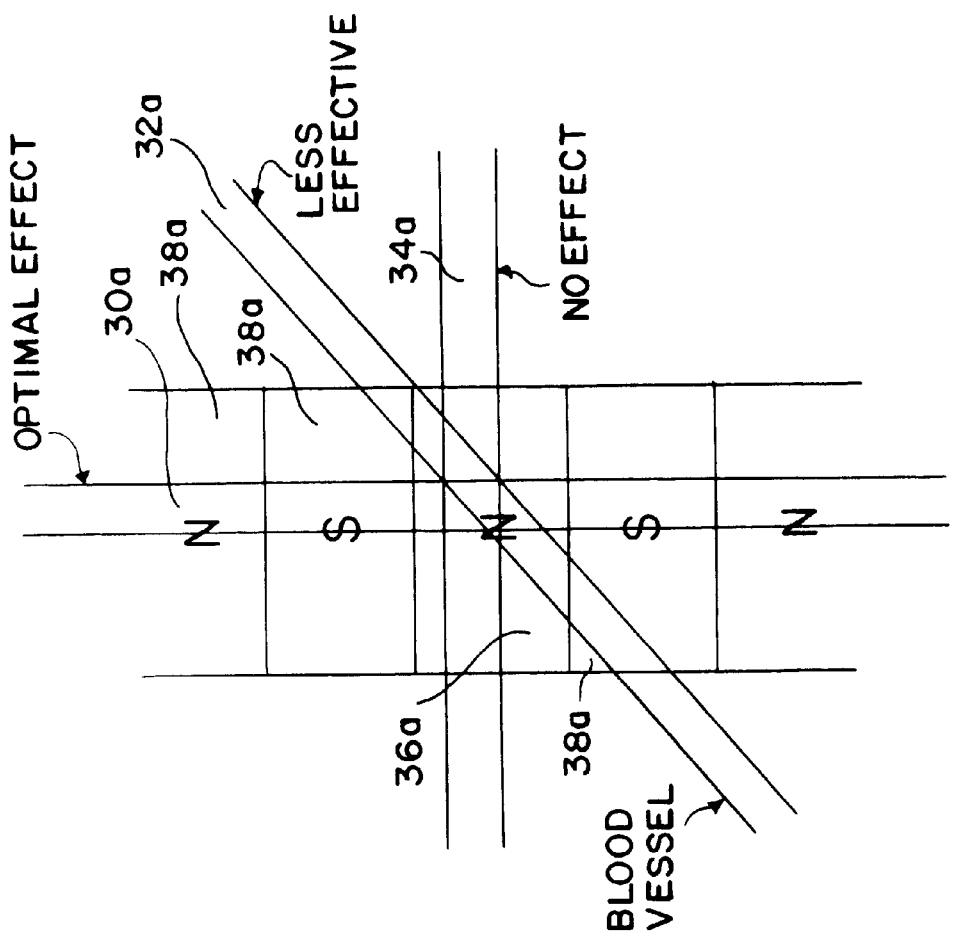
FIG. 4 is a top plan view of one embodiment of the prior art device as in FIG. 3, showing various positions of blood vessels traversing the prior art device as in FIG. 3 herein.
Figure 3:
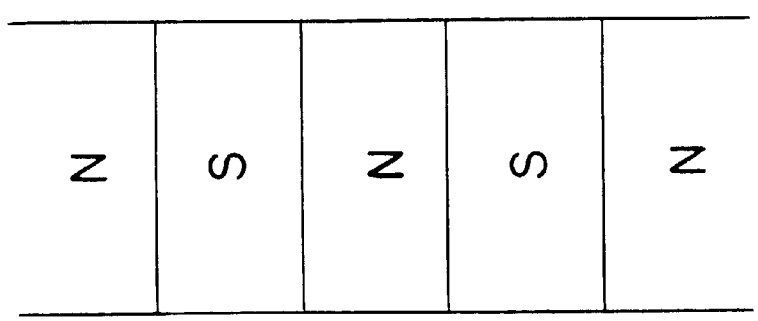
FIG. 3 is a top plan view of one embodiment of the prior art as noted in Latzke, U.S. Pat. No. 4,489,711.

As shown in FIG. 3, the prior art device of the Latzke '711 patent is made up of linear pole strips of alternating polarities, oriented in one direction. In FIG. 4, depicting the Latzke '711 prior art device, with various blood vessel orientations, blood vessel 30a will have an optimal effect, whereas blood vessel 32a will be less effective because it does not directly contact alternating polarities with the same effect as blood vessel 30a. For example, while the blood vessel 32a traverses the entire north polarity strip 36a, it barely touches the edge of south polarity strip 38a, therefore minimizing the effect of magnetic alternating poles upon the blood flow. Furthermore, as shown in FIG. 4, the blood vessel 34a, entirely traversing north polarity strip 36a, will have absolutely no therapeutic effect, since the blood vessel is not subject to alternating polarity zones.

Figure 6:
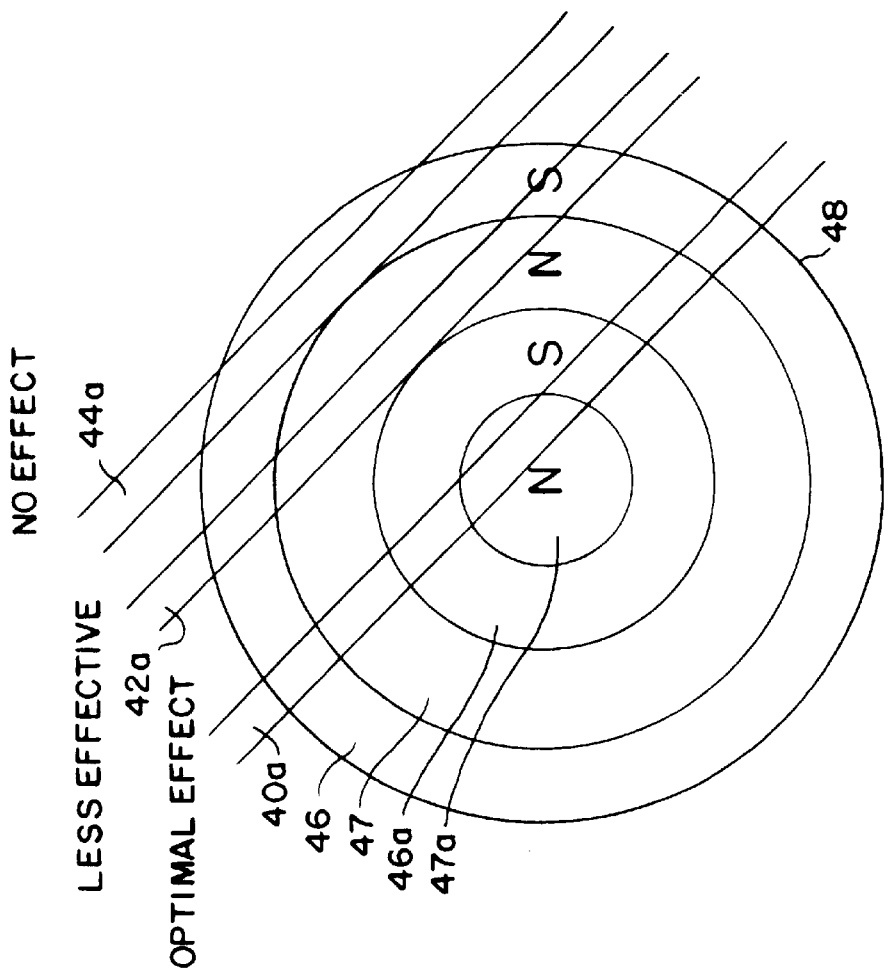
FIG. 6 is a top plan view of another embodiment of the prior art as shown in FIG. 5, showing various positions of blood vessels traversing the prior art device as in FIG. 5 herein.
Figure 5:
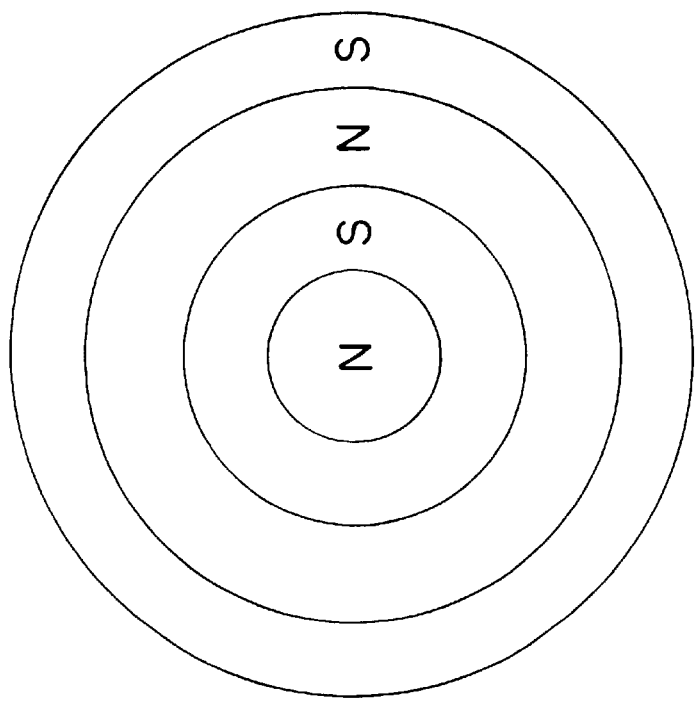
FIG. 5 is a top plan view of another embodiment of a prior art device, as noted in Baermann, U.S. Pat. No. 4,549,532, in drawing FIGS. 1, 3 and 4 therein.
Figure 8:
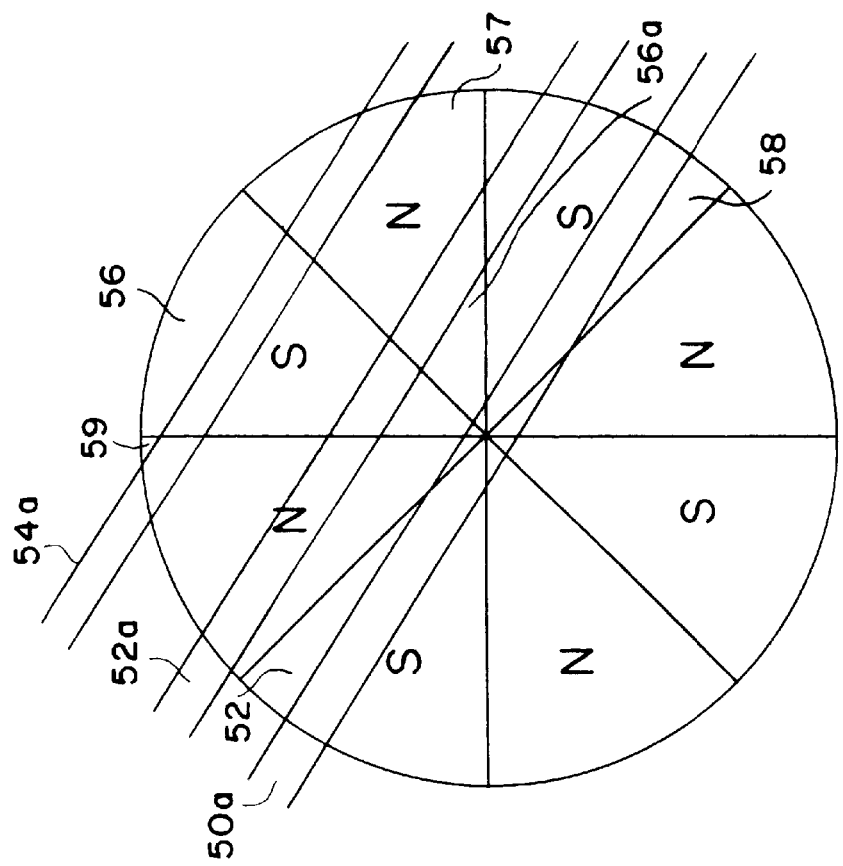
FIG. 8 is a top plan view of the prior art embodiment as shown in FIG. 7, showing various positions of blood vessels traversing the prior art device as in FIG. 7 herein.
Figure 7:
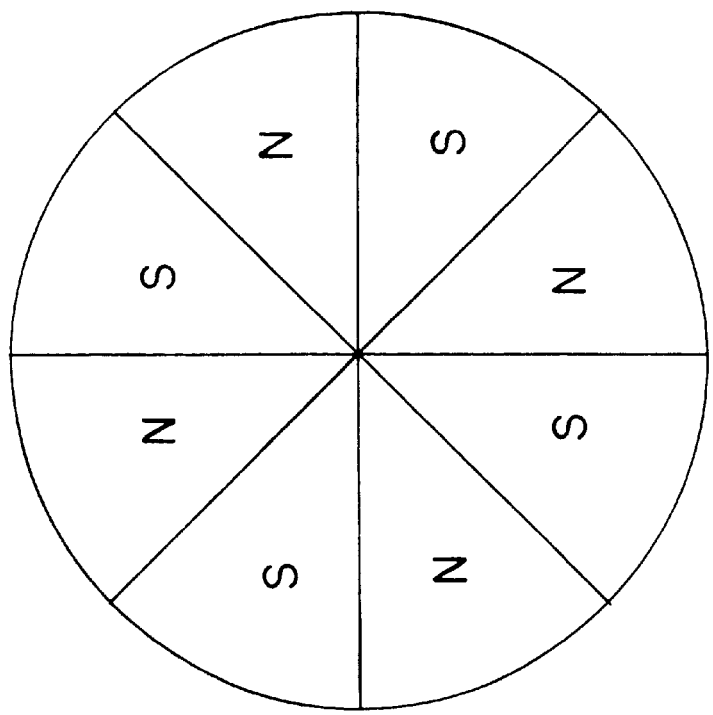
FIG. 7 is a top plan view of another embodiment of the prior art, as noted in Baerman, U.S. Pat. No. 4,549,532, in drawing FIG. 2 therein.

As shown in FIG. 5, there is noted a device as similar to that in the Baermann '532 patent with concentric rings of alternating polarities. As shown in FIG. 6, three blood vessels 40a, 42a and 44a are oriented in the same fashion as the blood vessels shown in FIG. 2. Blood vessel 40a will receive an optimal effect since it crosses several alternating poles. Blood vessel 42a will receive less of an effect since most of blood vessel 42a crosses north polarity ring 47, and little of south polarity ring 46 in relation to north polarity ring 47. Furthermore, blood vessel 44a will receive no therapeutic effect since it does not traverse any alternating polarity zones, but passes across only polarity ring 46 at the periphery of the device. An alternate view is shown in FIG. 7 and FIG. 8 for the specific embodiment as shown in FIG. 2 of the Baermann '532 device. This device has a reverse effect to that shown in FIG. 6 herein. As shown in FIG. 8, blood vessels 50a, 52a, and 54a traverse at the center, midway and the periphery of the device respectively. On the periphery, blood vessel 54a will be in contact with alternating polarities 56, 57, and 59 in a relatively uniform manner and therefore receive the desired effect. However the blood vessel 52a traversing midway between the center and the periphery will have less effect since the poles vary in width beyond an acceptable range. Furthermore, when blood vessel 50a traverses the center of the pad, it will substantially cross only two pie-shaped sector poles 57 and 58 of the same polarity, therefore it will have no therapeutic effect.

Figures 9, 10, 11:
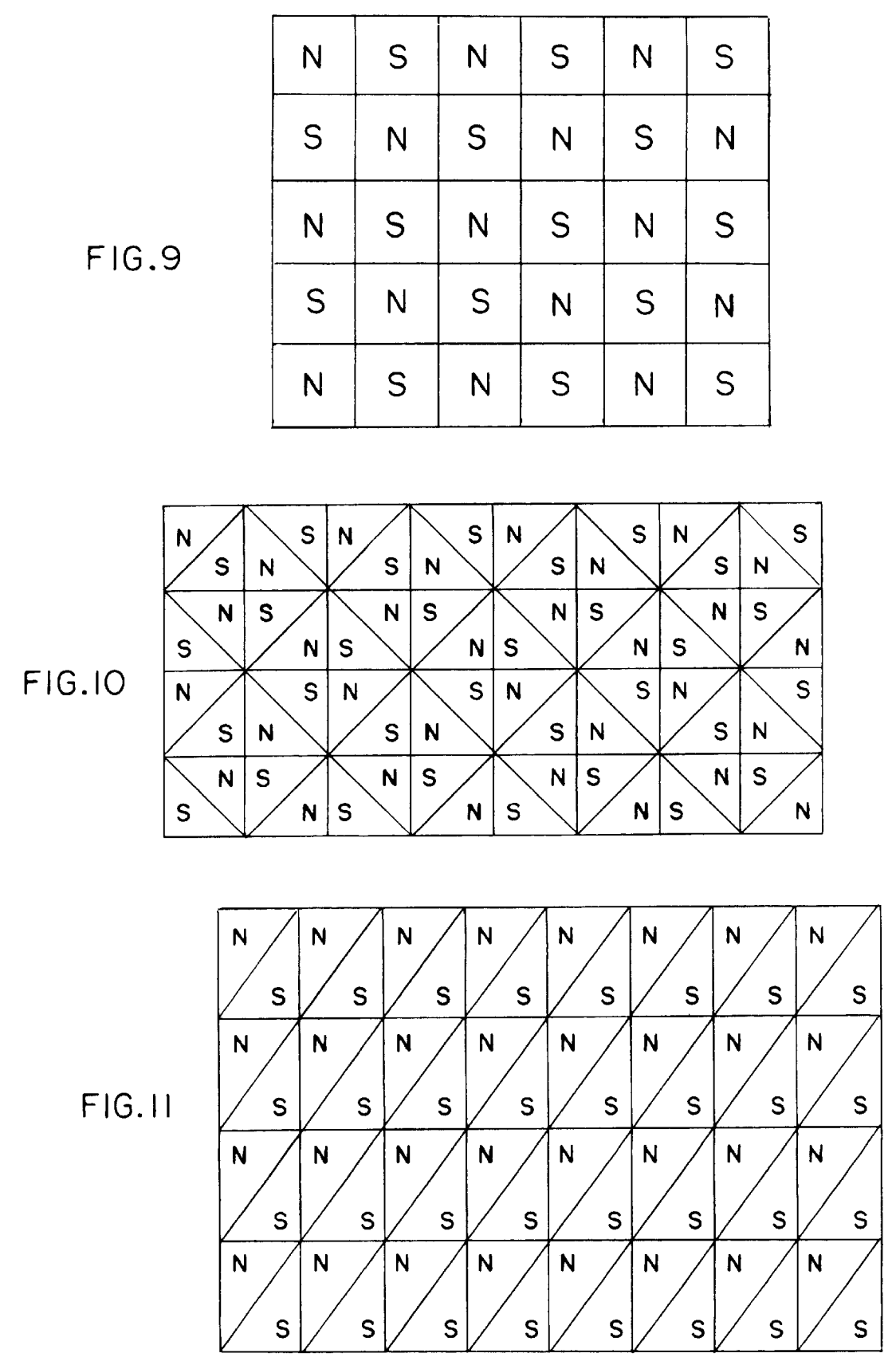

As noted in FIG. 9, the present invention may also be constructed in an alternate checkerboard pattern, wherein polarity zones of the same polarity are positioned in a staggered arrangement in the checkerboard pattern.

As illustrated in FIG. 9, magnetic zones of north polarity and magnetic zones of south polarity are positioned contiguous one another with each magnetic zone of north polarity being contiguous with four zones of south polarity and with each magnetic zone of south polarity being contiguous with four zones of north polarity (except for those magnetic zones positioned along the perimeter of the flexible pad.)

FIGS. 10 and 11 illustrate an embodiment of the present invention wherein magnetic zones of north polarity are contiguous with three zones of south polarity and vice versa.

In contrast to the prior art devices as shown in FIGS. 3 through 8 herein, the present invention as shown in FIGS. 1, 2 and 9 herein maximizes the therapeutic effects on blood vessels by increasing the blood flow, by virtue of the exposure of the blood vessels to constantly alternating polarity zones throughout the various configurations of the present invention.

It is to be noted that other variations and modifications may be made to the present invention without departing from the spirit and scope thereof, as noted in the appended claims.

I claim:

1. A flexible magnetic pad for therapeutic use, comprising:

a flexible pad having an active surface including permanent magnetic particles embedded therein with said magnetic particles forming at least one magnetic zone of north polarity and a plurality of magnetic zones of south polarity;

said at least one magnetic zone of north polarity and said plurality of magnetic zones of south polarity being positioned contiguous with one another; and, said at least one magnetic zone of north polarity being contiguous with at least three of said zones of south polarity, wherein said at least one magnetic zone of north polarity varies in size relative to said plurality of magnetic zones of south polarity.

2. The flexible magnetic pad for therapeutic use according to claim 1, wherein said magnetic zones of south polarity are each between 4 mm–10 mm in width.

3. The flexible magnetic pad for therapeutic use according to claim 1, wherein said magnetic zones of south polarity are each four-sided in shape.

4. A flexible magnetic pad for therapeutic use, comprising:

a flexible pad having an active surface including permanent magnetic particles embedded therein with said magnetic particles forming at least one magnetic zone of south polarity and a plurality of magnetic zones of north polarity;

said at least one magnetic zone of south polarity and said plurality of magnetic zones of north polarity being positioned contiguous with one another; and, said at least one magnetic zone of south polarity being contiguous with at least three of said zones of north polarity, wherein said at least one magnetic zone of south polarity varies in size relative to said plurality of magnetic zones of north polarity.

5. The flexible magnetic pad for therapeutic use according to claim 4, wherein said magnetic zones of north polarity are each between 4 mm–10 mm in width.

6. The flexible magnetic pad for therapeutic use according to claim 4, wherein said magnetic zones of south polarity are each four-sided in shape.

7. A flexible magnetic pad for therapeutic use, comprising:

a flexible pad having an active surface including permanent magnetic particles embedded therein with said magnetic particles forming at least one magnetic zone of north polarity and a plurality of magnetic zones of south polarity;

said at least one magnetic zone of north polarity and said plurality of magnetic zones of south polarity being positioned contiguous with one another; and, said at least one magnetic zone of north polarity being contiguous with at least four of said zones of south polarity, wherein said at least one magnetic zone of north polarity varies in size relative to said plurality of magnetic zones of south polarity.

8. The flexible magnetic pad for therapeutic use according to claim 7, wherein said magnetic zones of north polarity are each between 4 mm–10 mm in width.

9. The flexible magnetic pad for therapeutic use according to claim 7, wherein said magnetic zones of north polarity are each four-sided in shape.

10. A flexible magnetic pad for therapeutic use, comprising:

a flexible pad having an active surface including permanent magnetic particles embedded therein with said magnetic particles forming at least one magnetic zone of south polarity and a plurality of magnetic zones of north polarity;

said at least one magnetic zone of south polarity and said plurality of magnetic zones of north polarity being positioned contiguous with one another; and, said at least one magnetic zone of south polarity being contiguous with at least four of said zones of north polarity, wherein said at least one magnetic zone of south polarity varies in size relative to said plurality of magnetic zones of north polarity.

11. The flexible magnetic pad for therapeutic use according to claim 10, wherein said magnetic zones of south polarity are each between 4 mm–10 mm in width.

12. The flexible magnetic pad for therapeutic use according to claim 10, wherein said magnetic zones of south polarity are each four-sided in shape.

13. A flexible pad for therapeutic use by direct application upon a human body, comprising a flexible pad having an active surface with permanent magnetic particles embedded therein with said magnetic particles forming contiguous north and south polarity zones, said north and south polarity zones forming a spiral pattern of alternating polarities emanating from generally the center of the pad.

* * * * *